United States Patent [19]

Warriner

[11] Plant 4,650

[45] Feb. 17, 1981

[54] ROSE PLANT

[75] Inventor: William A. Warriner, Tustin, Calif.

[73] Assignee: Jackson & Perkins Co., Medford, Oreg.

[21] Appl. No.: 90,659

[22] Filed: Nov. 2, 1979

[51] Int. Cl.[3] ..... A01H 5/00
[52] U.S. Cl. ..... Plt./15
[58] Field of Search ..... Plt./15

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

Rose plant of hybrid tea class resulting from cross of unnamed cultivar with pollen of South Seas, U.S. Plant Pat. No. 2,184. Plant is vigorous, more upright than South Seas. Blossom color is Wilson's Sulphur Yellow in bud and Mimosa Yellow when fully open.

1 Drawing Figure

This present invention relates to a new and distinct cultivar of rose plant of the hybrid tea class which was originated by me by crossing an unnamed cultivar with pollen of the cultivar South Seas, U.S. Plant Pat. No. 2,184.

The primary objective of this breeding was to produce a new rose cultivar of the hybrid tea class, combining the vigor and foliage characteristics of the parent South Seas with the yellow flower color of the seed parent. This objective was substantially achieved along with other desirable improvements as evidenced by the following unique combination of characteristics which are outstanding in the new cultivar and which distinguish it from its parents as well as all other cultivars of which I am aware:

1. An upright, vigorous plant, more upright in habit than its pollen parent South Seas.
2. Large foliage.
3. Stiff petals that open very slowly on the plant.
4. Light yellow flower color closely resembling Wilson's Sulphur Yellow in the bud and Mimosa Yellow when fully open.
5. Very little fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart except where ordinary dictionary significance of color is indicated.

Parentage:
- *Seed parent.*—Unnamed variety.
- *Pollen parent.*—South Seas.

Classification:
- *Botanical.*—Rosa hybrid.
- *Commercial.*—Hybrid tea.

FLOWER

Observations made from specimens grown outside at Irvine, Calif., in November of 1978.

Blooming habit: Continuous.

Bud:
- *Size.*—1" to 1⅛" when petals start to unfurl.
- *Form.*—Short, broad base.
- *Color.*—When sepals first divide, Near Sulphur Yellow (⅓); when half blown, upper side of petals Sulphur Yellow (½); lower side of petals varying between Sulphur Yellow (⅓) and (½) with occasional streak of green.
- *Sepals.*—Color: Outer surface Scheeles Green (860/3); inner surface Scheeles Green (860/3) with much tomentum; three appendaged sepals lightly appendaged; two unappendaged sepals, hairy edged with a few stipitate glands.
- *Receptacle.*—Color: Scheeles Green (860/3). Shape: Deep funnel. Size: Large, long. Surface: Smooth.
- *Peduncle.*—Length: Short. Surface: Smooth. Color: Light green. Strength: Stiff, erect.
- *Opening.*—Petals fold out with little quilling until flower ages.

Bloom:
- *Size.*—Large. Average open size 4" to 4½".
- *Borne.*—Mostly singly.
- *Stems.*—Long, strong.
- *Form.*—When first open, high centered. Permanence: Retains its form to the end.
- *Petalage.*—Number of petals under normal conditions: 30.
- *Color.*—Center of flower: Upper side of petals Near Mimosa Yellow (602/1). Reverse side of petals Near Mimosa Yellow (602/1). Base of petals Mimosa Yellow (602). General tonality from a distance: Mimosa Yellow (602/1).
- *Variegations.*—None.
- *Discoloration.*—General tonality at end of first day, no change; third day, lightens to Mimosa Yellow (602/3).
- *Fragrance.*—Very slight.

Petals:
- *Texture.*—Thick.
- *Shape.*—Round.
- *Form.*—Tips slightly recurved.
- *Arrangement.*—Imbricated. Petaloids in center, few, large.
- *Persistence.*—Drop off cleanly.

*Lastingness.*—On the plant, long. As cut flower, long.

Reproductive parts:

*Anthers.*—Large, many. Color, yellow. Arrangement, regular around styles.

*Filaments.*—Color: Yellow.

*Pollen.*—Lemon yellow.

*Styles.*—Color: Near White.

*Stigmas.*—Color: White.

PLANT

Form: Bush.

Growth: Very vigorous, upright, branching.

Foliage: Number of leaflets on normal mid-stem leaves: Mostly 5.

*Size.*—Large.

*Quantity.*—Normal.

*Color.*—New foliage: Light green, near Scheeles Green (860/3) overlaid partially with Garnette Brown (00918/3). Old foliage: Near Spinach Green (0960).

Leaflets:

*Shape.*—Wide oval.

*Texture.*—Leathery.

*Edge.*—Serrated.

*Serrations.*—Single, small.

*Petiole.*—Rachis: Color, reddish. Underside: Prickles.

*Stipules.*—Long, nearly smooth.

*Disease resistance.*—Normally resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, few. On laterals from stalk, few.

*Form.*—Long base, hooked downward.

*Color when young.*—Green and red.

*Position.*—Irregular.

Small prickles:

*Quantity.*—On main stalks, none. On laterals, none.

I claim:

1. A new and distinct cultivar of rose plant of the hybrid tea class, substantially as herein shown and described, characterized particularly as to novelty by the unique combination of its vigorous, upright habit of growth, relatively large foliage, bud color of Wilson's Sulphur Yellow aging to Mimosa Yellow, very light fragrance.

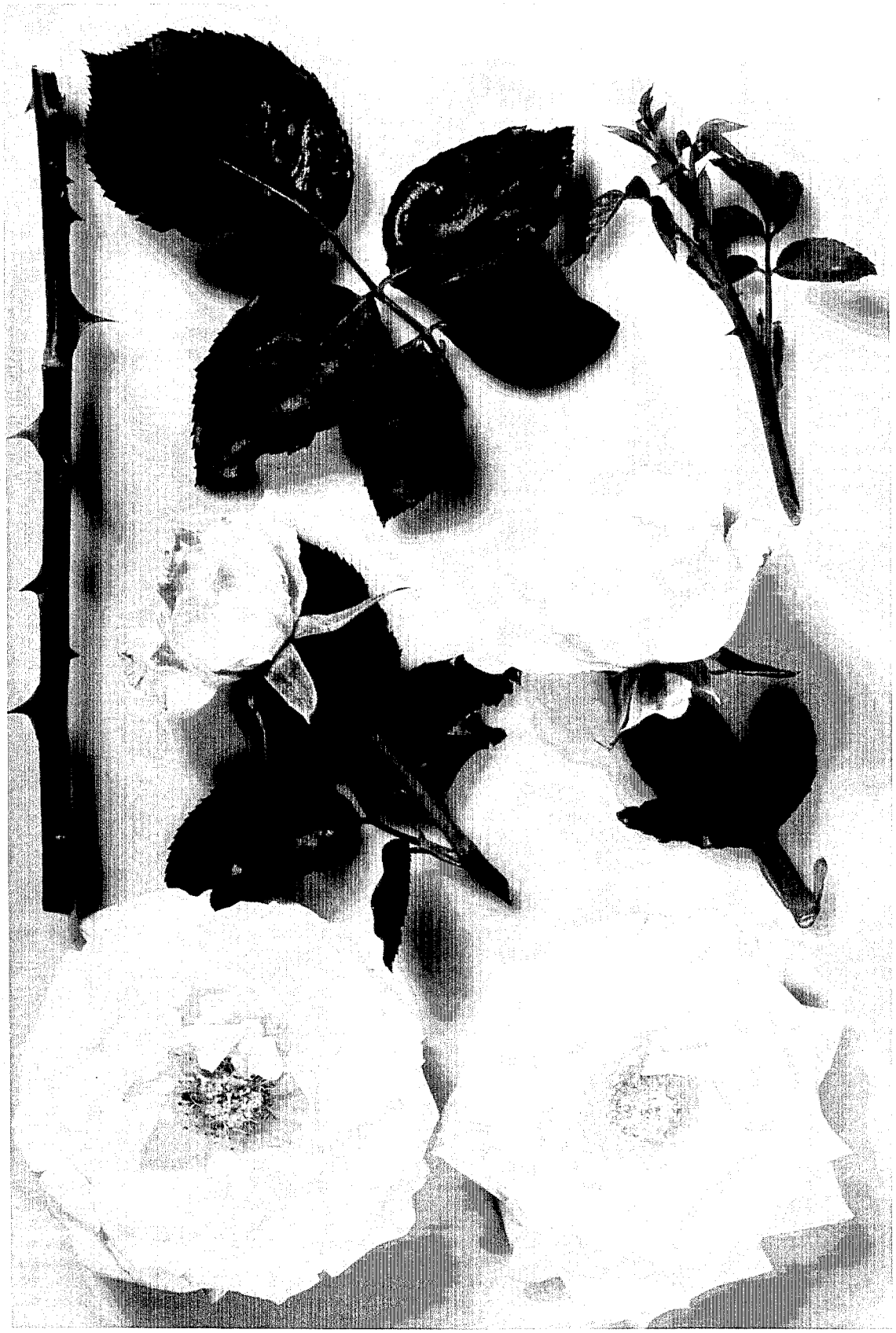

* * * * *